(12) United States Patent
Komatsu et al.

(10) Patent No.: US 8,487,136 B2
(45) Date of Patent: Jul. 16, 2013

(54) METHOD FOR PRODUCING NORBORNENE DERIVATIVE

(75) Inventors: Shinichi Komatsu, Yokohama (JP); Toshikatsu Shoko, Yokohama (JP); Tadahiro Kaminade, Yokohama (JP)

(73) Assignee: Nippon Oil Corporation, Minato-ku, Tokyo (JP)

( * ) Notice: Subject to any disclaimer, the term of this patent is extended or adjusted under 35 U.S.C. 154(b) by 481 days.

(21) Appl. No.: 12/669,954

(22) PCT Filed: Jul. 29, 2008

(86) PCT No.: PCT/JP2008/063548
§ 371 (c)(1),
(2), (4) Date: Jan. 20, 2010

(87) PCT Pub. No.: WO2009/017100
PCT Pub. Date: Feb. 5, 2009

(65) Prior Publication Data
US 2010/0197970 A1    Aug. 5, 2010

(30) Foreign Application Priority Data

Jul. 30, 2007  (JP) .................................. 2007-197295
Jun. 27, 2008  (JP) .................................. 2008-169339

(51) Int. Cl.
*C07F 9/02* (2006.01)
*C07F 15/00* (2006.01)
*C07F 17/02* (2006.01)
*C07C 22/00* (2006.01)

(52) U.S. Cl.
USPC ................ 568/17; 556/16; 556/136; 570/182

(58) Field of Classification Search
None
See application file for complete search history.

(56) References Cited

U.S. PATENT DOCUMENTS 6,294,706 B1    9/2001  Bergstrom et al.
2006/0173186 A1*  8/2006  Buchwald et al. ................. 546/2

FOREIGN PATENT DOCUMENTS

| JP | 2002-114716 A | 4/2002 |
| WO | WO97/33848 | 9/1997 |
| WO | WO 01/07449 A1 | 2/2001 |

OTHER PUBLICATIONS

Shaulis, K. et al., "Tandem Suzuki coupling—norbornadiene insertion reactions. A convenient route to 5,6-diarylnorbornene compounds," J.Org.Chem. (2002) 67:5860-3.*
Mayo, P. et al. "Palladium-catalyzed hydrophenylation of bicyclic alkenes," Tetrahedron (2002) 58: 9527-40.*
Anderson, K. et al. "General catalysts for the Suzuki-Miyaura and Sonogashira coupling reactions of aryl chlorides and for the coupling of challenging substrate combinations in water," Angew. Chem.Int. Ed. (2005) 44: 6173-7.*
Motti, E. et al. "Catalytic dehydrogenation of o-alkylated or o-alkoxylated iodoarenes with concomitant hydrogenolysis," Adv. Synth.Catal. (2008) 350: 565-569.*
Brunner, H. et al. "Asymmetric catalysis. 72. Enantioselective hydroarylation of norbornene and norbornadiene with palladium (II) acetate/phosphine catalysts," Synthesis (1991) 12: 1121-4.*
Arcadi, A. et al. "Palladium-catalyzed preparation of exo-aryl derivatives of the norbornane skeleton," J. Orgmet. Chem. (1989) 368: 249-56.*
Li, C. et al. "Synthesis of nortricyclenes from norbornadiene using palladium complexes and zinc powder," J.Chem.Soc., Chem. Comm. (1990) 1774-1775.*
Li, C. et al. "Synthesis and reactivities of intramolecular eta-2-arene and alkene species via insertion of norbornadiene into palladium-carbon bonds. Preparation of 3,5-disubstituted nortricyclenes from these complexes," Organometallics, (1993) 12: 3945-3954.*
International Search Report dated Oct. 21, 2008.
Wu, X. et al., "Asymmetric hydroarylation of Norbornene derivatives catalyzed by palladium complexes of chiral quinolinyl-oxazolines, Tetrahedron Asymmetry", 2001, vol. 12, pp. 2565-2569.
Yuan, K. et al., "A Highly Efficient Palladacycle Catalyst for Hydrophenylation of C-, N-, and O-Substituted Bicyclic Alkenes under Aerobic Condition," J. Org. Chem., 2005, vol. 70, No. 15, pp. 6085-6088.
Bravo, J. et al., "Synthesis, characterization and catalytic activity in Heck-type reactions of orthometallated $Pd^{II}$ and $Pt^{III}$ complexes derived from (1R, 2R)-1, 2-diaminocyclohexane," Journal of Organometallic Chemistry, 2002, vol. 650, pp. 157-172.
Larock, Richard C. and Johnson, Peter L., "Palladium-catalysed Intermolecular Arylation and Alkenylation of Bicyclic Alkenes," J. Chem. Soc., Commun., 1989, p. 1368.

* cited by examiner

Primary Examiner — Porfirio Nazario Gonzalez
Assistant Examiner — James Meadows
(74) Attorney, Agent, or Firm — Fitch, Even, Tabin & Flannery, LLP

(57) ABSTRACT

A method for selectively producing a monoaryl norbornene derivative represented by a formula (5) involves having a norbornadiene derivative represented by a formula (3) and a bromine compound represented by a formula (4) react with each other in the presence of a reducing agent, palladium and at least one selected from phosphorus compounds represented by the formulas (1) and (2), whereby the norbornene derivative represented by formula (5) having a monoaryl substituent is an exo configuration.

14 Claims, 9 Drawing Sheets

US 8,487,136 B2

METHOD FOR PRODUCING NORBORNENE DERIVATIVE

CROSS-REFERENCE TO RELATED APPLICATIONS

This Application is the U.S. national phase application under 35 U.S.C. 371 of International Application No. PCT/JP2008/063548, filed Jul. 29, 2008, which designated the United States, and claims foreign priority from Japanese Patent Application No.: JP 2007-197295, filed Jul. 30, 2007, and Japanese Patent Application No. JP2008-169339, filed Jun. 27, 2008, the entire disclosures of the aforesaid applications are hereby incorporated herein by reference in their entirety for all purposes.

TECHNICAL FIELD

The present invention relates to a method for producing a norbornene derivative.

BACKGROUND OF THE INVENTION

Cyclic olefin-based polymers produced by using cyclic olefins as monomers have alicyclic structures in their main skeletons. Hence, such a cyclic olefin-based polymer is more likely to be amorphous, exhibits an excellent transparency and heat resistance, has a small photo-elastic coefficient, and also has such properties as a low water absorbing property, acid resistance, alkaline resistance, and a high electrical insulation property. For this reason, use of the cyclic olefin-based polymers has been examined in applications such as display applications (retardation films, diffusion films, liquid-crystal substrates, films for touch panels, light guide plates, protection films for polarizing plates, and the like), optical lens applications, optical disk applications (CD, MD, CD-R, DVD, and the like), optical fiber applications, optical film/sheet applications, and sealing applications for optical semiconductors. Particularly, out of such cyclic olefin-based polymers, hydrogenated products of cyclic olefin-based polymers obtained by ring opening metathesis polymerization of norbornene derivatives are known to exhibit an excellent transparency and heat resistance, and to have a characteristic of a small photo-elastic constant. Hence, such a hydrogenated product, as well as polycarbonate, has been used as retardation films for liquid crystal displays (LCD) and the like. For this reason, development of cyclic olefin-based polymers obtained by using norbornene derivatives has been in progress in recent years.

Under such circumstances, various methods for producing norbornene derivatives which serve as raw materials of the cyclic olefin-based polymers have been studied. For example, International Application Japanese-Phase Publication No. 2000-506183 (Document 1) discloses a method for producing a norbornene derivative using the Diels-Alder reaction, in which a cyclic diene is reacted with an olefinic compound to yield a norbornene compound, wherein the cyclic diene is added gradually during the reaction. However, when the method for producing a norbornene derivative using the Diels-Alder reaction as described in Document 1 is used as a method for producing a norbornene derivative having a phenyl group at the 5-position, the obtained norbornene derivative is a mixture of an endo isomer in which the configuration of the phenyl group is an endo configuration and an exo isomer in which the configuration of the phenyl group is an exo configuration (endo:exo=6 to 8:4 to 2, such a ratio varies depending on reaction temperature). Accordingly, the exo isomer is not able to be produced selectively. In addition, such an endo isomer and an exo isomer have almost no difference in stability. Hence, even when isomerization by subjecting the obtained mixture to heat, or an acid or base catalyst is attempted, it is not possible to obtain only the exo isomer. Note that a conventional method for producing a norbornene derivative using the Diels-Alder reaction is shown in the following Reaction Formula (I):

[Reaction Formula (I)]

[Chemical Formula 1]

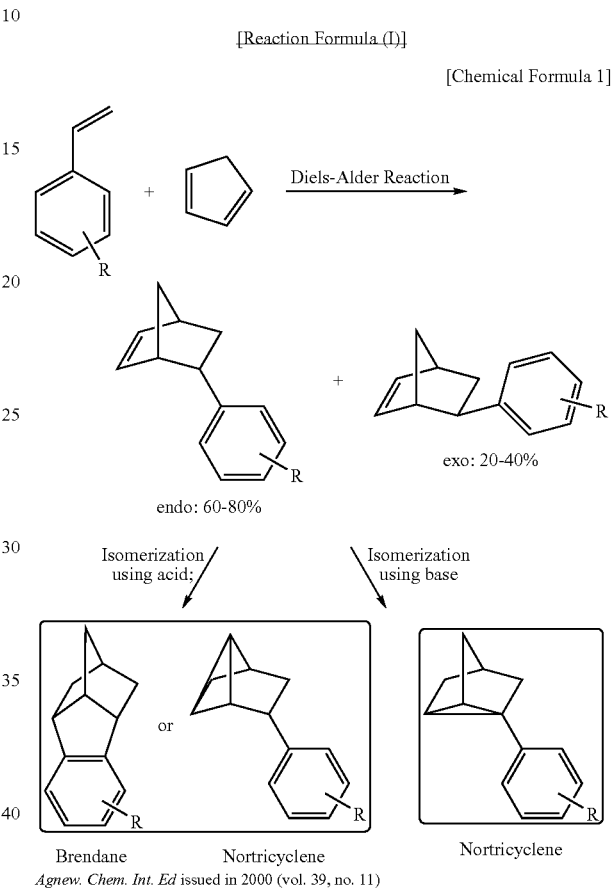

Agnew. Chem. Int. Ed issued in 2000 (vol. 39, no. 11)

pp. 1946 to 1949 (Document 2) discloses a method for obtaining a 5-phenyl 2-norbornene derivative. In this method, in the presence of a catalyst formed from palladium and a phosphorus compound represented by the following General Formula (6):

[Chemical Formula 2]

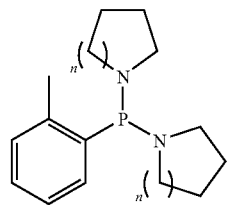

(in Formula (6), n represents 1 or 2),
a norbornadiene-based compound and a compound represented by the formula: X—R (in the formula, X represents a halogen, and R represents a phenyl group) are reacted with each other to form the 5-phenyl-2-norbornene derivative. The method for producing a norbornene derivative as described in Non-Patent Document 1 is capable of selectively producing a norbornene derivative at a high yield where the configuration of the phenyl group (a substituent at the 5-position) is an exo configuration. However, according to the method for producing a norbornene derivative as described in Document 2, when a substituted phenyl group having a substituent such as a t-butyl group or the like is attempted to be introduced as a substituent at the 5-position, a norbornene derivative in which the configuration of the substituted phenyl group is an exo configuration is not able to be produced at a high yield.

Moreover, J. CHEM. SOC., CHEM. COMMUN. issued in 1989 pp. 1368 to 1370 (Document 3) discloses a method for producing a norbornene derivative. In this method, by using palladium acetate, tetra-n-butylammonium chloride and potassium formate as a catalyst system, a norbornadiene and a phenyl iodide are reacted with each other to obtain a norbornene derivative. However, by the method for producing a norbornene derivative as described in Document 3, the reaction does not proceed at all when a phenyl bromide is used as a reactant instead of the phenyl iodide.

DISCLOSURE OF THE INVENTION

The present invention has been made in view of the problems of the conventional techniques. An object of the present invention is to provide a method for producing a norbornene derivative capable of selectively producing, at a sufficiently high yield, a specific norbornene derivative (an exo isomer) in which the configuration of a substituent such as a substituted phenyl group is an exo configuration.

The present inventors have earnestly studied in order to achieve the above object. As a result, the present inventors have found that a norbornene derivative represented by the following General Formula (5), in which the configuration of the substituent Z in the following General Formula (5) is an exo configuration, can be produced selectively at a sufficiently high yield in the following manner. Specifically, in the presence of palladium and at least one selected from phosphorus compounds represented by the following General Formulae (1) and (2), a norbornadiene derivative represented by the following General Formula (3) and a bromine compound represented by the following General Formula (4) are reacted with each other to thereby produce the norbornene derivative. This finding has led the inventors to complete the present invention.

A method for producing a norbornene derivative of the present invention is a method wherein, in the presence of palladium and at least one selected from phosphorus compounds represented by the following General Formulae (1) and (2):

[Chemical Formula 3]

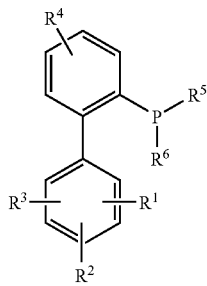

(1)

[in General Formula (1), $R^1$, $R^2$, $R^3$ and $R^4$ each independently represent anyone selected from an hydrogen atom, a linear chain saturated hydrocarbon group having 1 to 10 carbon atoms, a branched chain saturated hydrocarbon group having 3 to 10 carbon atoms, a cyclic saturated hydrocarbon group having 3 to 8 carbon atoms, a dialkylamino group having 1 to 10 carbon atoms, an alkoxy group having 1 to 10 carbon atoms and an alkali metal sulfonate group, and $R^5$ and $R^6$ each independently represents any one selected from a branched chain saturated hydrocarbon group having 3 to 10 carbon atoms, a cyclic saturated hydrocarbon group having 3 to 8 carbon atoms, a phenyl group, a tolyl group, a biphenyl group and a naphthyl group], and

[Chemical Formula 4]

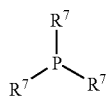

(2)

[in General Formula (2), $R^7$ represents a branched chain saturated hydrocarbon group having 3 to 10 carbon atoms], a norbornadiene derivative represented by the following General Formula (3):

[Chemical Formula 5]

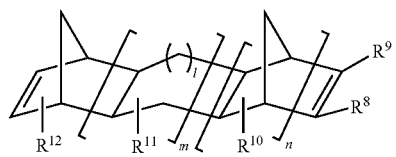

(3)

[in General Formula (3), $R^8$, $R^9$, $R^{10}$, $R^{11}$ and $R^{12}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms, l represents an integer of 0 or 1, m represents an integer of 0 or 1, and n represents an integer of 0 or 1], and a bromine compound represented by the following General Formula (4):

[Chemical Formula 6]

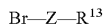

Br—Z—$R^{13}$ (4)

[in General Formula (4), Z represents anyone selected from a phenylene group, a naphthylene group and a biphenylene group, and $R^{13}$ represents any one selected from a hydrogen atom, a fluorine atom, a chlorine atom, a linear chain hydrocarbon group having 1 to 10 carbon atoms and a branched chain hydrocarbon group having 3 to 10 carbon atoms] are reacted with each other to thereby obtain a norbornene derivative represented by the following General Formula (5)

[Chemical Formula 7]

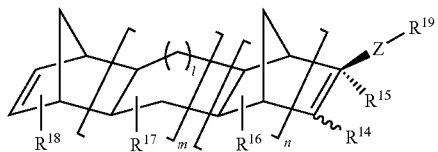

(5)

[in General Formula (5), $R^{14}$, $R^{15}$, $R^{16}$, $R^{17}$ and $R^{18}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms, Z represents any one selected from a phenylene group, a naphthylene group and a biphenylene group, $R^{19}$ represents any one selected from a hydrogen atom, a fluorine atom, a chlorine atom, a linear chain hydrocarbon group having 1 to 10 carbon atoms and a branched chain hydrocarbon group having 3 to 10 carbon atoms, l represents an integer of 0 or 1, m represents an integer of 0 or 1, and n represents an integer of 0 or 1], the norbornene derivative having a configuration of a substituent represented by Z in General Formula (5) that is an exo configuration.

In the method for producing a norbornene derivative of the present invention, it is preferable that, in General Formula (1), $R^1$, $R^2$, and $R^3$ are each independently any one selected from a linear chain saturated hydrocarbon group having 1 to 3 carbon atoms, an alkoxy group having 1 to 3 carbon atoms and an alkali metal sulfonate group, $R^4$ is a hydrogen atom, and $R^5$ and $R^6$ are each independently a cyclic saturated hydrocarbon group having 5 to 8 carbon atoms.

Further, in the method for producing a norbornene derivative of the present invention, it is preferable that, in General Formula (2), $R^7$ are each independently a branched chain saturated hydrocarbon group having 3 to 5 carbon atoms.

Moreover, in the method for producing a norbornene derivative of the present invention, it is preferable that, in each of General Formulae (3) and (5), m is 0, and n is 0.

Furthermore, in the method for producing a norbornene derivative of the present invention, it is preferable that Z in General Formula (4) is a phenylene group, $R^{13}$ in General Formula (4) is a branched chain hydrocarbon group having 3 to 5 carbon atoms, Z in General Formula (5) is a phenylene group, and $R^{19}$ in General Formula (5) is a branched chain hydrocarbon group having 3 to 5 carbon atoms.

In the method for producing a norbornene derivative of the present invention, it is preferable that, a base is further coexisted, when the norbornadiene derivative and the bromine compound are reacted with each other. As such a base, at least one selected from an alkali metal salt and an alkali metal hydroxide is preferable, and at least one selected from NaOH, $Na_2CO_3$, KOH and $K_2CO_3$ is more preferable. The use of such a base makes it possible to more sufficiently suppress the production of by-products, and to more efficiently produce a target norbornene derivative.

In the method for producing a norbornene derivative of the present invention, it is preferable that a content of the base is an amount that a molar ratio ([the base]:[the bromine compound]) of the content of the base to a content of the bromine compound is in a range from 1:1 to 10:1.

According to the present invention, it is possible to provide a method for producing a norbornene derivative capable of selectively producing, at a sufficiently high yield, a specific norbornene derivative (an exo isomer) in which the configuration of a substituent such as a substituted phenyl group is an exo configuration.

Note that, according to such a method for producing a norbornene derivative of the present invention, it is possible to simplify production process for the specific norbornene derivative (the exo isomer), and hence it is also possible to produce the specific norbornene derivative (the exo isomer) at a low cost.

DETAILED DESCRIPTION OF THE PREFERRED EMBODIMENTS

Figure 1:
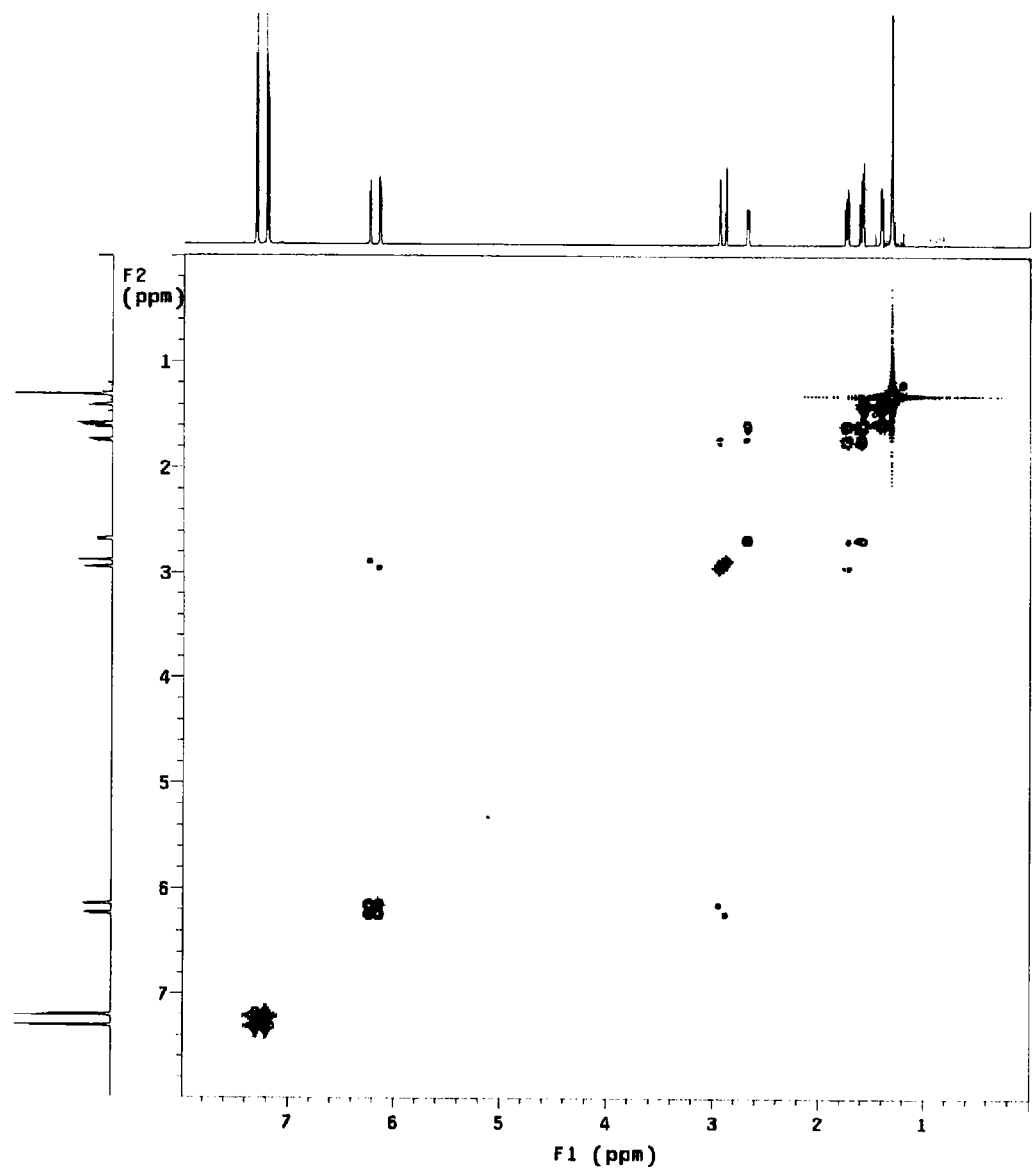
FIG. 1 is a graph of a two dimensional NMR spectrum of Compound A obtained in Example 1.

Hereinafter, the present invention will be described in detail on the basis of preferred embodiments thereof.

A method for producing a norbornene derivative of the present invention is a method wherein, in the presence of palladium and at least one selected from phosphorus compounds represented by the above-described General Formula (1) and (2), a norbornadiene derivative represented by the above-described General Formula (3) and a compound represented by the above-described General Formula (4) are reacted with each other to thereby obtain a norbornene derivative represented by the above-described General Formula (5), the norbornene derivative having a configuration of a substituent represented by Z in the above-described General Formula (5) that is an exo configuration.

First, the compounds used in the present invention will be described. An example of the phosphorus compound used in the present invention is a phosphorus compound represented by the following General Formula (1):

[Chemical Formula 8]

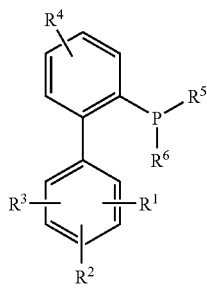

(1)

In General Formula (1), $R^3$, $R^2$, $R^3$ and $R^4$ each independently represent any one selected from an hydrogen atom, a linear chain saturated hydrocarbon group having 1 to 10 carbon atoms, a branched chain saturated hydrocarbon group having 3 to 10 carbon atoms, a cyclic saturated hydrocarbon group having 3 to 8 carbon atoms, a dialkylamino group having 1 to 10 carbon atoms, an alkoxy group having 1 to 10 carbon atoms and an alkali metal sulfonate group.

In the linear chain saturated hydrocarbon group having 1 to 10 carbon atoms which can be selected as such $R^1$, $R^2$, $R^3$ or $R^4$, one having 1 to 5 carbon atoms is preferable, and one having 1 to 3 carbon atoms is more preferable. If the number of the carbon atoms exceeds the upper limit, the yield of the norbornene derivative (exo-norbornene derivative) tends to be lowered, the norbornene derivative represented by the above-described General Formula (5), in which the configuration of the substituent represented by Z in the above-described General Formula (5) is an exo configuration. Examples of such a linear chain saturated hydrocarbon group having 1 to 10 carbon atoms include a methyl group, an ethyl group, a propyl group and the like.

In the branched chain saturated hydrocarbon group having 3 to 10 carbon atoms which can be selected as such $R^1$, $R^2$, $R^3$ or $R^4$, one having 3 to 7 carbon atoms is preferable, and one having 3 to 5 carbon atoms is more preferable. If the number of the carbon atoms exceeds the upper limit, the yield of the exo-norbornene derivative tends to be lowered. Examples of such a branched chain saturated hydrocarbon group having 3 to 10 carbon atoms include a t-butyl group and the like.

In the cyclic saturated hydrocarbon group having 3 to 8 carbon atoms which can be selected as $R^1$, $R^2$, $R^3$ or $R^4$, one having 5 to 7 carbon atoms is preferable. If the number of the carbon atoms exceeds the upper limit, the yield of the exo-norbornene derivative tends to be lowered. Examples of such a cyclic saturated hydrocarbon group include cycloalkyl groups such as a cyclopentyl group, cyclohexyl, and cycloheptyl groups.

In the dialkylamino group having 1 to 10 carbon atoms which can be selected as $R^1$, $R^2$, $R^3$ or $R^4$, one having 1 to 5 carbon atoms is preferable, and one having 1 to 3 carbon atoms is more preferable. If the number of the carbon atoms exceeds the upper limit, the yield of the exo-norbornene derivative tends to be lowered. Note that, in such a dialkylamino group, an alkyl group bonded to an amino group may be a linear chain alkyl group or a branched chain alkyl group, and is more preferably a linear chain alkyl group.

In the alkoxy group having 1 to 10 carbon atoms which can be selected as $R^1$, $R^2$, $R^3$ or $R^4$, one having 1 to 5 carbon atoms is preferable, and one having 1 to 3 carbon atoms is more preferable. If the number of the carbon atoms exceeds the upper limit, the yield of the exo-norbornene derivative tends to be lowered.

In the alkali metal sulfonate group which can be selected as $R^1$, $R^2$, $R^3$ or $R^4$, one containing sodium as the alkali metal is more preferable, from the viewpoint of easiness in synthesis and purification.

In the above-described General Formula (1), $R^1$, $R^2$, $R^3$ and $R^4$ are preferably each independently any one of a hydrogen atom, a linear chain saturated hydrocarbon group having 1 to 10 carbon atoms, an alkali metal sulfonate group and an alkoxy group having 1 to 10 carbon atoms, from the viewpoint of easiness in synthesis and purification. Moreover, as the phosphorus compound represented by the above-described General Formula (1), preferable is one whose $R^1$, $R^2$ and $R^3$ are each independently anyone selected from a linear chain saturated hydrocarbon group having 1 to 3 carbon atoms (particularly preferably a methyl group), an alkoxy group having 1 to 3 carbon atoms (particularly preferably a methoxy group) and an alkali metal sulfonate group, and whose $R^4$ is a hydrogen atom.

Moreover, $R^5$ and $R^6$ in the above-described General Formula (1) may be the same or different, and each are any one selected from a branched chain saturated hydrocarbon group having 3 to 10 carbon atoms, a cyclic saturated hydrocarbon group having 3 to 8 carbon atoms, a phenyl group, a tolyl group, a biphenyl group and a naphthyl group.

In the branched chain saturated hydrocarbon group having 3 to 10 carbon atoms which can be selected as such $R^5$ or $R^6$, one having 3 to 7 carbon atoms is preferable. If the number of the carbon atoms exceeds the upper limit, the yield of the exo-norbornene derivative tends to be lowered.

In the cyclic saturated hydrocarbon group having 3 to 8 carbon atoms which can be selected as $R^5$ or $R^6$, one having 5 to 8 carbon atoms is more preferable. If the number of the carbon atoms exceeds the upper limit, the yield of the exo-norbornene derivative tends to be lowered.

Moreover, each of $R^5$ and $R^6$ in the above-described General Formula (1) is more preferably a cyclic saturated hydrocarbon group having 5 to 8 carbon atoms (particularly preferably a cyclohexyl group), from the viewpoint of easiness in synthesis and purification.

Furthermore, an example of the phosphorus compound used in the present invention is a phosphorus compound represented by the following General Formula (2):

[Chemical Formula 9]

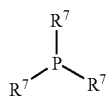

(2)

In the above-described General Formula (2), $R^7$s may be the same or different, and each are a branched chain saturated hydrocarbon group having 3 to 10 carbon atoms. Among such a branched chain saturated hydrocarbon group having 3 to 10 carbon atoms which can be selected as $R^7$, one having 3 to 7 carbon atoms is preferable, and one having 3 to 5 carbon atoms is more preferable. If the number of the carbon atoms exceeds the upper limit, the yield of the exo-norbornene derivative tends to be lowered. A t-butyl group is particularly preferable as such a saturated hydrocarbon group, from the viewpoint of yield and selectivity.

Next, the palladium used in the present invention will be described. Such palladium is not particularly limited, but preferably used as a salt of palladium, from the viewpoint that a complex can easily be formed with the phosphorus compound serving as a ligand. Examples of such a salt of palladium include palladium acetate, palladium chloride, palladium nitrate, palladium bromide, palladium iodide, palladium cyanide, palladium sulfate, palladium acetylacetonate, palladium trifluoroacetate, palladium carbon and the like. Because the formation of the complex with the phosphorus compound (a ligand) is easier, palladium acetate, palladium acetylacetonate or the like is more preferable.

Next, the norbornadiene derivative according to the present invention will be described. Such a norbornadiene derivative is represented by the following General Formula (3):

[Chemical Formula 10]

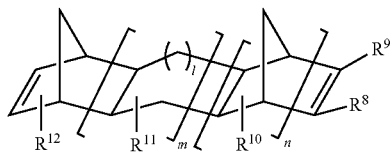

(3)

In General Formula (3), $R^8$, $R^9$, $R^{10}$, $R^{11}$ and $R^{12}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms.

In such a linear chain hydrocarbon group having 1 to 10 carbon atoms which can be selected as $R^8$, $R^9$, $R^{10}$, $R^{11}$, or $R^{12}$, one having 1 to 5 carbon atoms is preferable. If the number of the carbon atoms exceeds the upper limit, the yield of the exo-norbornene derivative tends to be lowered. Such a linear chain hydrocarbon group is preferably a linear chain saturated hydrocarbon group.

In the branched chain hydrocarbon group having 3 to 10 carbon atoms which can be selected as $R^8$, $R^9$, $R^{10}$, $R^{11}$ or $R^{12}$, one having 3 to 5 carbon atoms is preferable. If the number of the carbon atoms exceeds the upper limit, the yield of the exo-norbornene derivative tends to be lowered. Such a branched chain hydrocarbon group is preferably a branched chain saturated hydrocarbon group.

Such $R^8$, $R^9$, $R^{10}$, $R^{11}$ and $R^{12}$ each are more preferably a hydrogen atom, a fluorine atom or a chlorine atom, and further preferably a hydrogen atom, from the viewpoint of the yield of the exo-norbornene derivative.

In the above-described General Formula (3), l represents an integer of 0 or 1, m represents an integer of 0 or 1, and n represents an integer of 0 or 1. If such a value of m or n exceeds the upper limit, the following cases may occur. Specifically, in one case, the production of the norbornene derivative becomes difficult because of difficulty in purification or decrease in yield during the production. In another case, the obtained norbornene derivative has so high a glass transition temperature (Tg) that thermal processability in orientation process or the like is deteriorated. Moreover, from the viewpoint that a desired norbornene derivative can be obtained at a higher yield, it is preferable that the value of m be 0, and the value of n be 0. The value of l is preferably 0, from the viewpoint that such value allows a target product to be relatively easily synthesized.

Next, bromine compound represented by the following General Formula (4) will be described.

[Chemical Formula 11]

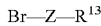

(4)

In General Formula (4), Z represents any one selected from a phenylene group, a naphthylene group and a biphenylene group. As such a Z, a phenylene group is particularly preferable, from the viewpoint of the yield of the exo-norbornene derivative.

In the above-described General Formula (4), $R^{13}$ is any one selected from a hydrogen atom, a fluorine atom, a chlorine atom, a linear chain hydrocarbon group having 1 to 10 carbon atoms and a branched chain hydrocarbon group having 3 to 10 carbon atoms.

In such a linear chain hydrocarbon group having 1 to 10 carbon atoms which can be selected as $R^{13}$, one having 1 to 5 carbon atoms is preferable. If the number of the carbon atoms exceeds the upper limit, the yield of the exo-norbornene derivative tends to be lowered. Moreover, such a linear chain hydrocarbon group is preferably a linear chain saturated hydrocarbon group.

In the branched chain hydrocarbon group having 3 to 10 carbon atoms which can be selected as $R^{13}$, one having 3 to 7 carbon atoms is preferable, and one having 3 to 5 carbon atoms is more preferable. If the number of the carbon atoms exceeds the upper limit, the yield of the exo-norbornene derivative tends to be lowered. Moreover, such a branched chain hydrocarbon group is preferably a branched chain saturated hydrocarbon group.

As the bromine compound represented by the following General Formula (4), preferable is one whose Z in the above-described General Formula (4) is a phenylene group, and whose $R^{13}$ in the above-described General Formula (4) is a branched chain hydrocarbon group having 3 to 5 carbon atoms (particularly preferably a t-butyl group), from the viewpoint of the yield of the exo-norbornene derivative.

Next, a step in which the norbornadiene derivative and the bromine compound are reacted with each other will be described. Such a step is a step in which, in the presence of the phosphorus compound and the palladium, the norbornadiene derivative and the bromine compound are reacted with each other. Such a reaction step makes use of a so-called reductive Heck reaction (hydroarylation reaction). Note that, the present inventors speculates that, in such a reaction step, the phosphorus compound and the palladium form a palladium complex in which the phosphorus compound serves as a ligand, and the norbornadiene derivative and the bromine compound are reacted with each other, with the palladium complex serving as a catalyst, thereby making it possible to selectively obtain the desired norbornene derivative.

The amount of the phosphorus compound represented by the above-described General Formula (1) used in such a reaction step varies depending on the kind of the phosphorus compound used and the like, and not particularly limited. However, it is preferable that the amount be equal to or larger than an amount which allows the palladium to be completely converted into a complex (a complex in which the phosphorus compound serves as a ligand), and it is more preferable that the content ratio of the phosphorus compound be in a range from 1 to 1000 mol to 1 mol of the palladium (in term of metal). Moreover, such a content of the phosphorus compound is preferably 10 to 0.00001% by mole, based on all the compounds in a reaction system. If such a content ratio of the phosphorus compound is less than the lower limit, the reaction rate tends to be reduced. Meanwhile, if such a content ratio exceeds the upper limit, side-reactions tend to increase.

The content of the norbornadiene derivative represented by the above-described General Formula (3) is preferably 0.1 to 50% by mole, and more preferably 1 to 20% by mole, based on all the compounds in a reaction system. If such a content of the norbornadiene derivative is less than the lower limit, the reaction rate tends to be reduced. Meanwhile, if such a content exceeds the upper limit, side-reactions tend to increase.

Regarding the content ratio between the norbornadiene derivative represented by the above-described General Formula (3) and the bromine compound represented by the above-described General Formula (4), a molar ratio ([the norbornadiene derivative]:[the bromine compound]) between the norbornadiene derivative represented by the above-described General Formula (3) and the bromine compound represented by the above-described General Formula (4) is preferably in a range from 20:1 to 1:1, and more preferably in a range from 10:1 to 2:1. If such a content ratio of the norbornadiene derivative is less than the lower limit, side-reactions tend to increase. Meanwhile, if such a content ratio exceeds the upper limit, the reaction rate tends to be reduced.

Moreover, the content of the palladium is preferably 0.0000001 to 10% by mole, and more preferably 0.000001 to 1% by mole, based on all the compounds in a reaction system. If such a content of the palladium is less than the lower limit, the reaction rate tends to be reduced. Meanwhile, if such a content exceeds the upper limit, side-reactions tend to increase.

In a reaction system, a ratio ([the palladium]:[the norbornadiene derivative]) between the molar amount of the palladium in terms of the metal and the molar amount of the norbornadiene derivative represented by the above-described General Formula (3) is preferably in a range from 0.00000001:1 to 0.1:1, and more preferably in a range from 0.0000001:1 to 0.001:1. If such an amount of the palladium used is less than the lower limit, the reaction rate tends to be reduced. Meanwhile, if such an amount exceeds the upper limit, side-reactions tend to increase.

In such a reaction step, it is preferable to use a solvent. A known organic solvent can be used as appropriate as such a solvent, as long as the solvent is capable of dissolving reactive substrate used such as the norbornadiene derivative and the compound represented by the above-described General Formula (4), the phosphorus compound used, and the like. Examples of such an organic solvent include aprotic polar solvents such as dimethylformamide, dimethylacetamide, N-methylpyrrolidone and dimethyl sulfoxide, ether based solvents such as tetrahydrofuran and dioxane, nitrile-based solvents such as acetonitrile and benzonitrile, aromatic-based solvents such as benzene, toluene, and xylene, and the like.

Moreover, the amount of such a solvent is preferably an amount that the concentration of all the reaction substrates in a reaction system becomes 0.1 to 2.0 mol/L, and more preferably an amount that the concentration of all the substrates in a reaction system becomes 0.2 to 1.0 mol/L. Regarding such an amount of the solvent used, if the concentration of all the substrates described above is less than the lower limit, the reaction rate tends to be reduced, and the conversion tends to be lowered. Meanwhile, if the concentration of all the substrates described above exceeds the upper limit, a reaction between norbornadiene derivatives tends to occur and by-products tend to be produced.

In such a reaction step, it is preferable that a reducing agent coexist, from the viewpoints that the reaction can proceed more efficiently, and that the production of the by-product can be more efficiently inhibited. Examples of such a reducing agent include zinc; sodium borohydride; formic acid; alkali metal salts of formic acid such as lithium formate, sodium formate, potassium formate, rubidium formate and cesium formate; alkaline earth metal salts of formic acid such as magnesium formate, calcium formate, strontium formate and barium formate; ammonium salts of formic acid such as ammonium formate; metal salts of formic acid such as zinc formate, and iron formate; and the like.

The content of such a reducing agent is preferably an amount that a molar ratio ([the reducing agent]:[the bromine compound]) to the content of the bromine compound is in a range from 1:1 to 1:10, and more preferably an amount that the molar ratio ([the reducing agent]:[the bromine compound]) is in a range from 1:1 to 1:5. If such a content of the reducing agent is less than the lower limit, the conversion tends to be lowered. Meanwhile, if such a content of the reducing agent exceeds the upper limit, a by-product (norbornane) tends to be produced by hydrogenation of a norbornene which is the target product.

Moreover, in such a reaction step, in order to neutralize a hydrogen halide generated by reacting the norbornadiene derivative represented by the above-described General Formula (3) with the bromine compound represented by the above-described General Formula (4), it is preferable that a base is coexisted as a neutralizer. Such a base is not particularly limited, and an organic base, an inorganic base, or the like can be used as the base. Examples of the base include trialkylamines such as trimethylamine, triethylamine, tripropylamine and tributylamine; pyridines such as pyridine and dimethylaminopyridine; inorganic hydroxides such as sodium hydroxide, potassium hydroxide and calcium hydroxide; alkali carbonates such as sodium carbonate, potassium carbonate, cesium carbonate, and calcium carbonate; metal alkoxides such as sodium methoxide, sodium ethoxide, and potassium t-butoxide; and the like.

Among those bases, from the viewpoint that production of by-products can be inhibited more sufficiently, it is preferable to use at least one selected from the group consisting of alkali metal salts and alkali metal hydroxides. As the alkali metal salt, an alkali metal carbonate is more preferable. Moreover, as the base described above, at least one selected from sodium hydroxide (NaOH), sodium carbonate ($Na_2CO_3$), potassium hydroxide (KOH) and potassium carbonate ($K_2CO_3$) is more preferable, because production of by-products can be more highly inhibited. At least one selected from KOH and $K_2CO_3$ is further preferable. Among those, KOH is particularly preferable from the viewpoint that the target norbornene derivative can be produced at a higher yield.

Moreover, the content of such a base is preferably an amount that a molar ratio ([the base]:[the bromine compound]) to the content of the bromine compound is in a range from 1:1 to 1:10, and more preferably an amount that the molar ratio is in a range from 1:1 to 1:5. If such a content of the base is less than the lower limit, the conversion tends to be lowered and by-products tend to increase. Meanwhile, if such a content exceeds the upper limit, the reaction rate tends to be reduced, and the yield tends to be lowered.

A temperature condition for such a reaction step is preferable in a range from 20 to 180° C., more preferably in a range from 60 to 150° C., and further preferably in a range from 80 to 140° C., and normally particularly preferably in a range from 80 to 120° C. If such a reaction temperature is lower than the lower limit, the reaction rate tends to be reduced, and the conversion tends to be lowered. Meanwhile, if such a reaction temperature exceeds the upper limit, the reaction between norbornadiene derivative molecules tends to occur, and by-products tend to be produced.

The reaction time for such a reaction is preferably 0.1 to 100 hours, and more preferably in a range from 1 to 20 hours. If such reaction time is less than the lower limit, there is a tendency that the conversion is lowered and hence the product cannot be obtained in a high yield. Meanwhile, if such reaction time exceeds the upper limit, there is a tendency that the palladium and the ligand (the phosphorus compound) are likely to be deactivated by oxygen and hence a phenomenon in which the conversion levels off is observed.

As described above, by reacting the norbornadiene derivative represented by the above-described General Formula (3) with the bromine compound represented by the above-described General Formula (4) in the presence of the palladium and at least one selected from the phosphorus compounds represented by the above-described General Formulae (1) and (2), it is possible to selectively produce a norbornene derivative (exo-norbornene derivative) represented by the following General Formula (5):

[Chemical Formula 12]

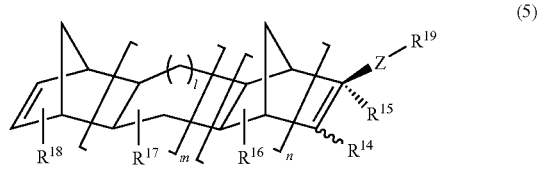

(5)

[in General Formula (5), $R^{14}$, $R^{15}$, $R^{16}$, $R^{17}$ and $R^{18}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms, Z represents any one selected from a phenylene group, a naphthylene group and a biphenylene group, $R^{19}$ represents any one selected from a hydrogen atom, a fluorine atom, a chlorine atom, a linear chain hydrocarbon group having 1 to 10 carbon atoms and a branched chain hydrocarbon group having 3 to 10 carbon atoms, l represents an integer of 0 or 1, m represents an integer of 0 or 1, and n represents an integer of 0 or 1], wherein a configuration of a substituent Z in General Formula (5) is an exo configuration. Note that, it is not known exactly why the exo-norbornene derivative can be selectively produced according to the present invention. However, the present inventors speculate as follows. Specifically, the present invention makes use of a hydroarylation reaction in which, in the presence of the phosphorus compound (ligand) and the palladium, the norbornadiene derivative and the bromine compound are reacted with each other. Moreover, in the present invention, the combination of the palladium and the phosphorus compound (ligand) results in formation of a palladium complex catalyst suitable for the selective production of the exo isomer. After that, in the presence of the complex catalyst, it is possible that the reaction between the norbornadiene derivative and the bromine compound is progressed. The present inventors speculate that, for the above-described reason, the exo isomer is selectively produced.

In the above-described General Formula (5), $R^{14}$, $R^{15}$, $R^{16}$, $R^{17}$ and $R^{18}$ each independently are any one selected from a hydrogen atom, a fluorine atom, a chlorine atom, a linear chain hydrocarbon group having 1 to 10 carbon atoms and a branched chain hydrocarbon group having 3 to 10 carbon atoms. In the above-described General Formula (5), l represents an integer of 0 or 1, m represents an integer of 0 or 1, and n represents an integer of 0 or 1.

Moreover, in the above-described General Formula (5), $R^{14}$, $R^{15}$, $R^{16}$, $R^{17}$, $R^{18}$, l, m, and n are respectively the same as $R^8$, $R^9$, $R^{10}$, $R^{11}$, $R^{12}$, l, m, and n in the above-described General Formula (3). In the above-described General Formula (5), Z is the same as Z in the above-described General Formula (4). Moreover, in the above-described General Formula (5), $R^{19}$ is the same as $R^{13}$ in the above-described General Formula (4).

Regarding the exo-norbornene derivative represented by the above-described General Formula (5), it is more preferable that, in the above-described General Formula (5), m be 0 and n be 0, from the viewpoints that the exo-norbornene derivative can be produced relatively easily, and that a film of a polymer obtained by ring opening polymerization of the exo-norbornene derivative can be provided with both negative A characteristics and heat resistance.

Regarding the exo-norbornene derivative represented by the above-described General Formula (5), it is preferable that Z be a phenylene group and that $R^{19}$ be a branched chain hydrocarbon group having 3 to 5 carbon atoms (particularly preferably a t-butyl group) from the viewpoint that moderate negative A characteristics and practical heat resistance can be expressed.

Moreover, examples of the exo-norbornene derivative represented by the above-described General Formula (5) include exo-norbornene derivatives represented by the following General Formulae (i) to (xv). Note that in each of the following General Formulae (i) to (xv), the configuration of the substituted phenyl group or the substituted naphthyl groups is an exo configuration.

[Chemical Formula 13]

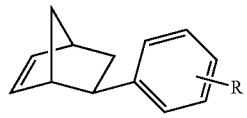

(i)

R: H, F, Cl, Me, Et, n-Pr, i-Pr, n-Bu, sec-Bu, t-Bu

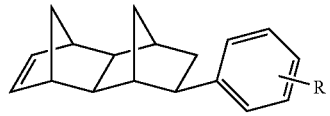

(ii)

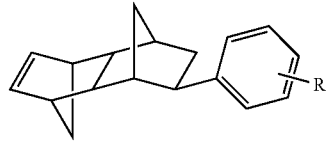

(iii)

R: H, F, Cl, Me, Et, n-Pr, i-Pr, n-Bu, sec-Bu, t-Bu

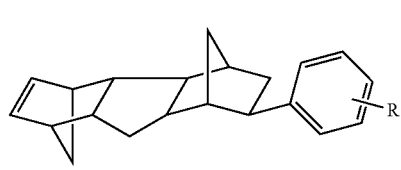

(iv)

(v)

R: H, F, Cl, Me, Et, n-Pr, i-Pr, n-Bu, sec-Bu, t-Bu

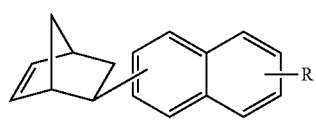

(vi)

R: H, F, Cl, Me, Et, n-Pr, i-Pr, n-Bu, sec-Bu, t-Bu

-continued (vii)
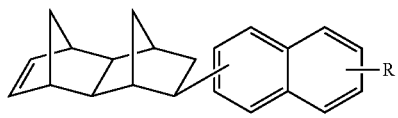
R: H, F, Cl, Me, Et, n-Pr, i-Pr, n-Bu, sec-Bu, t-Bu (viii)
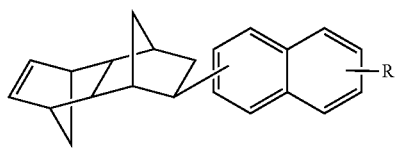
R: H, F, Cl, Me, Et, n-Pr, i-Pr, n-Bu, sec-Bu, t-Bu

[Chemical Formula 14]

(ix)
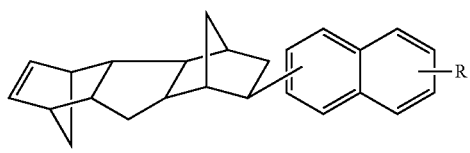

(x)
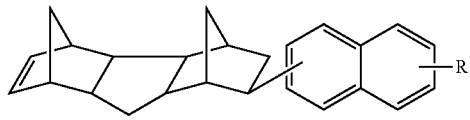
R: H, F, Cl, Me, Et, n-Pr, i-Pr, n-Bu, sec-Bu, t-Bu (xi)
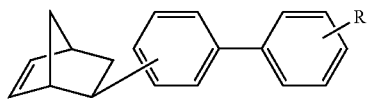
R: H, F, Cl, Me, Et, n-Pr, i-Pr, n-Bu, sec-Bu, t-Bu (xii)
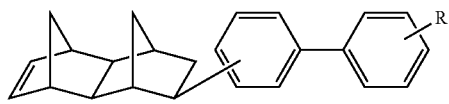

(xiii)
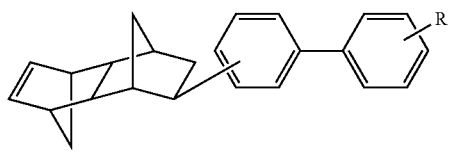
R: H, F, Cl, Me, Et, n-Pr, i-Pr, n-Bu, sec-Bu, t-Bu (xiv)
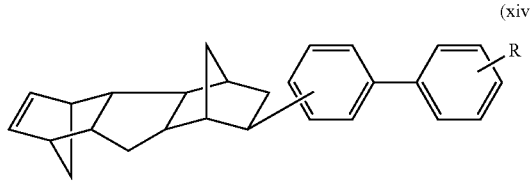

(xv)
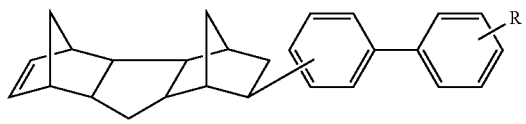
R: H, F, Cl, Me, Et, n-Pr, i-Pr, n-Bu, sec-Bu, t-Bu

The norbornene derivative obtained by employing the method for producing a norbornene derivative of the present invention can be converted into a desired polymer through a ring opening polymerization, a ring opening polymerization with a subsequent hydrogenation reaction, an addition polymerization, a radical polymerization, a cationic polymerization, an anionic polymerization, or the like. If necessary, such a norbornene derivative can be subjected to copolymerization reaction with any copolymerizable compound to obtain a copolymer. A polymer synthesized from such a norbornene derivative exhibits an excellent transparency, heat resistance and a low water absorbing property, and can be arbitrarily controlled in terms of magnitude of birefringence value and wavelength dispersibility thereof in accordance with its application. For this reason, a polymer synthesized from such a norbornene derivative can be suitably applied as a material for forming optical disks, magneto-optical discs, optical lenses (Fθ lenses, pickup lenses, lenses for laser printers, lenses for cameras, and the like), spectacle lenses, optical films and sheets (films for display, retardation films, polarizing films, protection films for polarizing plates, diffusion films, anti-reflection films, liquid-crystal substrates, EL substrates, substrates for electronic paper, substrates for touch panels, PDP front panels, and the like), substrates for transparent electro-conductive films, optical fibers, light guide plates, optical cards, optical mirrors, sealing materials for ICs, LSIs, and LEDs, and the like. In addition, since such a norbornene derivative is an exo isomer, use of such a norbornene derivative as a material for retardation films makes it possible to form a retardation film which has optical characteristics as a negative A being unique even among negative birefringence characteristics, a retardation film in which a birefringence wavelength dispersion characteristics is reverse dispersion, and the like.

EXAMPLES

Hereinafter, the present invention will be described more specifically on the basis of Examples and Comparative Examples. However, the present invention is not limited to the following Examples. Note that, hereinafter, the molecular structures of products obtained in Examples and Comparative Examples were identified by determining 1H and 13C-NMR, and two dimensional NMR (HH-COSY, CH-COSY, and DEPT) of each of the products obtained in Examples and Comparative Examples in deuterated chloroform by using superconducting nuclear magnetic resonance absorption apparatuses (NMR, manufactured by Varian, Inc., trade name: UNITY INOVA-600 and UNITY INOVA-400).

Example 1

First, into a 1.0-L three-necked flask, 2-dicyclohexylphosphino-2'-methylbiphenyl (a phosphorus compound: 258 mg: 0.708 mmol), palladium acetate (13.3 mg: 0.059 mmol), dimethyl sulfoxide (DMSO: 250 ml), norbornadiene (19.0 ml: 190 mmol), 4-tert-butylbromobenzene (10.0 ml: 59 mmol), triethylamine ($NEt_3$: 26.7 ml: 192 mmol), and formic acid (5.9 ml: 154 mmol) were fed under a nitrogen atmosphere, and then heated with stirring under a temperature condition of 80° C. for 4 hours, to thereby obtain a reaction solution. Note that, in such a reaction solution, the content ratio of palladium acetate to 4-tert-butylbromobenzene was 0.1% by mole, the content ratio of the phosphorus compound to 4-tert-butylbromobenzene was 1.2% by mole, the molar equivalent of norbornadiene to 4-tert-butylbromobenzene was 3.22 equivalent, the molar equivalent of $NEt_3$ to 4-tert-butylbromobenzene was 3.25 equivalent, and the molar equivalent of formic acid to 4-tert-butylbromobenzene was 2.61 equivalent.

Next, the reaction solution was cooled to 25° C., and then poured into 300 ml of ice water. By using a separatory funnel, extraction was performed with n-hexane (50 ml×3 times) to obtain a n-hexane solution. Subsequently, the n-hexane solution was washed with water and a saturated sodium chloride solution. Then, the washed n-hexane solution was dried with anhydrous magnesium sulfate, filtered and concentrated. Thus, a crude product (12.4 g) was obtained.

Thus obtained crude product was subjected to gas chromatography analysis. As a result, the crude product was found to be a mixture of exo-5-(p-tert-butylphenyl)bicyclo[2.2.1]-2-heptene (Compound A), endo-5-(p-tert-butylphenyl)tricyclo[2.2.1.0$^{2,6}$]heptane (Compound B) and tert-butylbenzene (Compound C). Note that the following Reaction Formula (II) shows the production step of such a crude product. Incidentally, Compound D in the following Reaction Formula (II) is endo-5-(p-tert-butylphenyl)bicyclo[2.2.1]-2-heptene.

[Reaction Formula (II)]

[Chemical Formula 15]

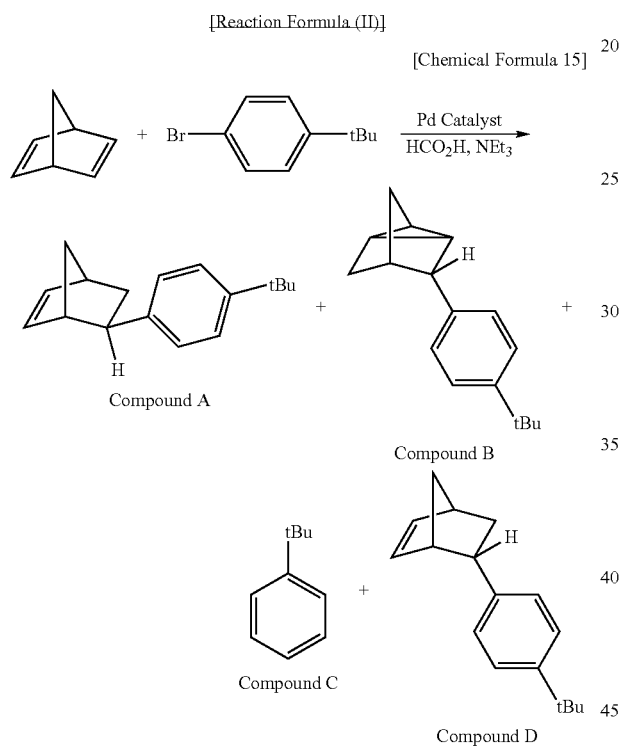

Next, the crude product was purified by distillation to obtain a product as a fraction at 104° C./1 mmHg. The amount of such a product yield was 11.7 g (yield: 87.1%). The product was subjected to gas chromatography analysis and NMR analysis. As a result, the product was found to be a mixture of Compound A (yield 80.60) and Compound B (yield 6.5%), and also was found to contain no Compound D. Thereafter, Compound A and Compound B were separated by using a recycling preparative HPLC (manufactured by Japan Analytical Industry Co., Ltd., LC-918). In such a separation step, recycling separation for about 20 hours was performed, whereby both were substantially completely separated from each other.

Figure 2:
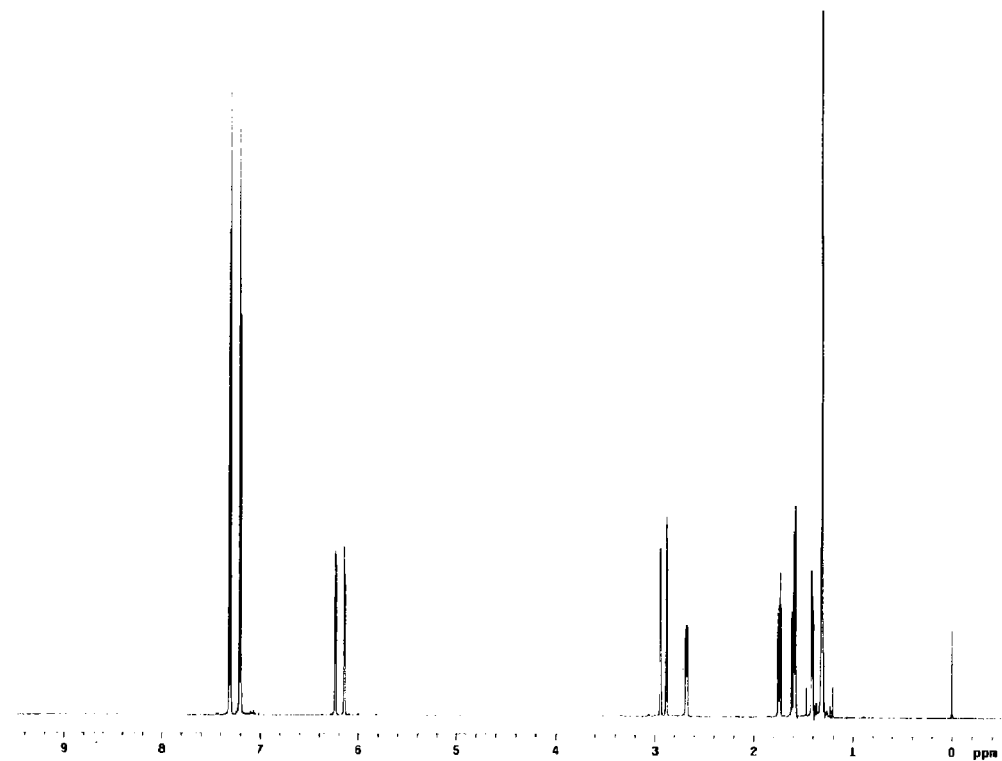
FIG. 2 is a graph of a $^1$H-NMR spectrum of Compound A obtained in Example 1.
Figure 3:
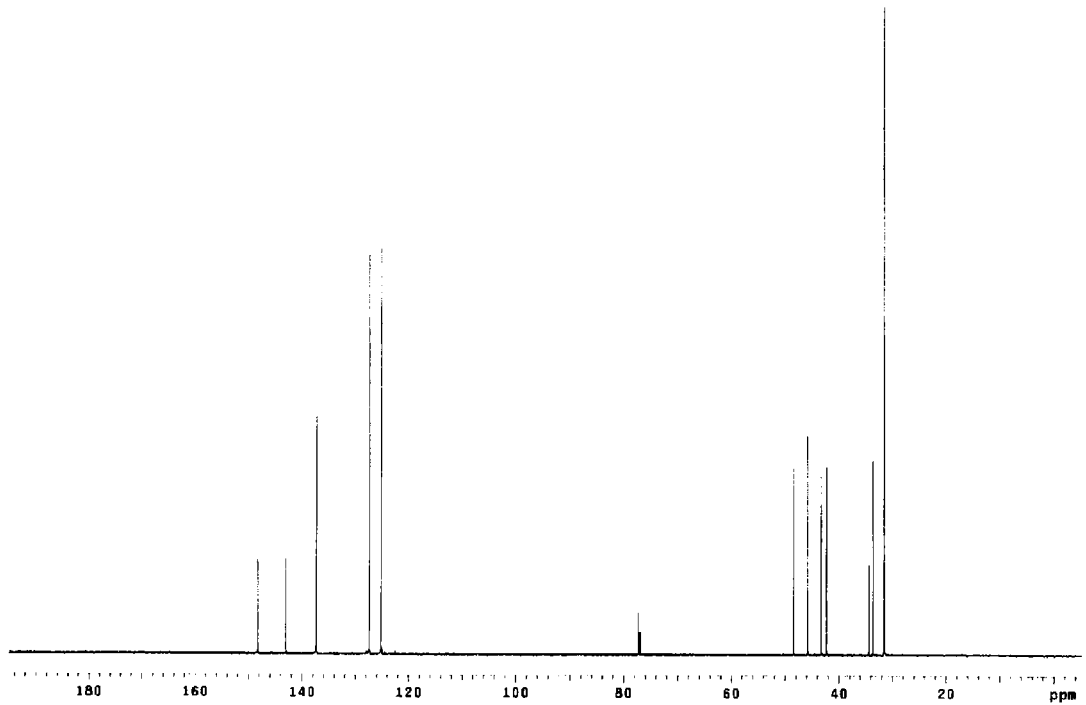
FIG. 3 is a graph of a $^{13}$C-NMR spectrum of Compound A obtained in Example 1.
Figure 4:
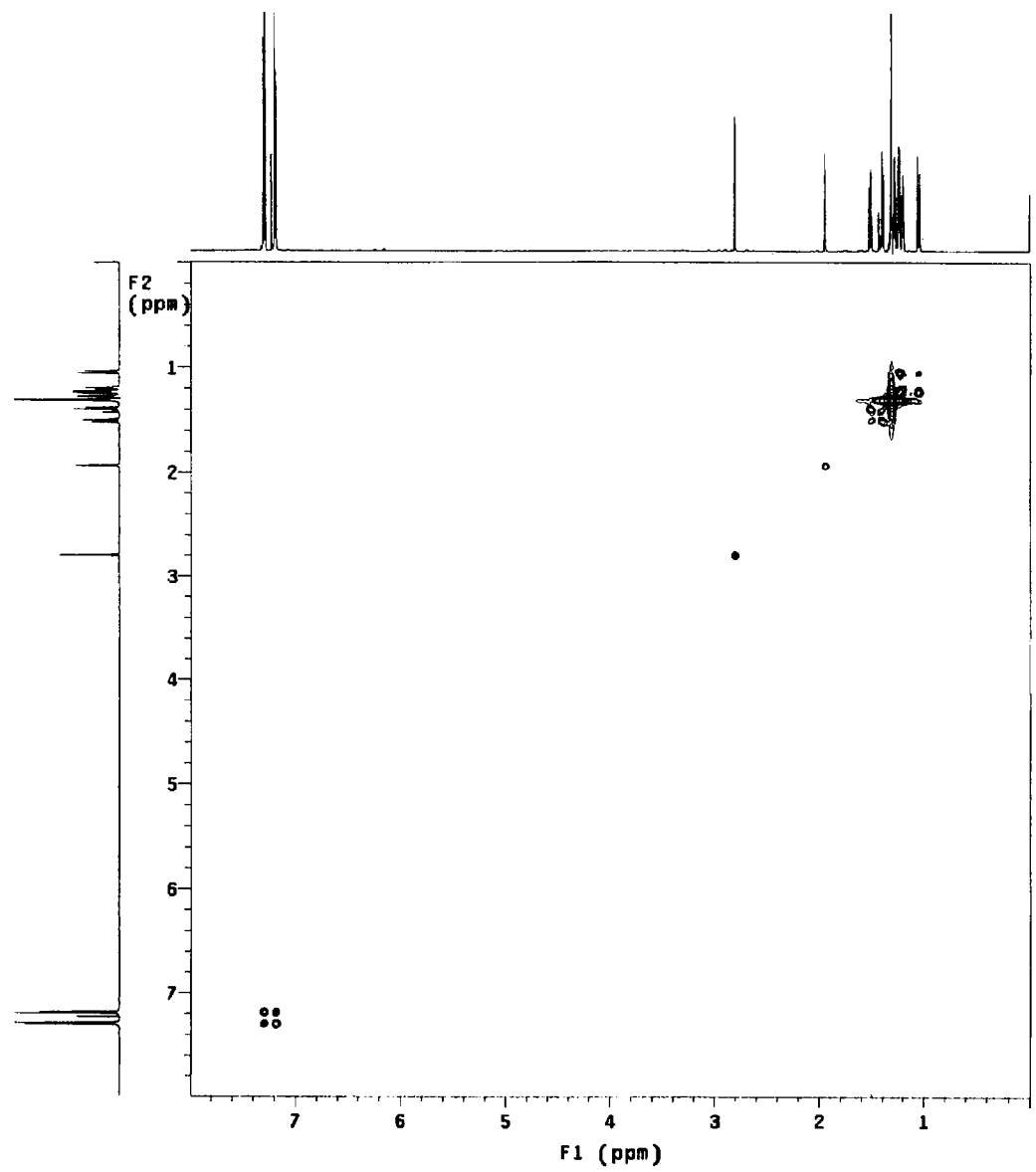
FIG. 4 is a graph of a two dimensional NMR spectrum of Compound B obtained in Example 1.
Figure 5:
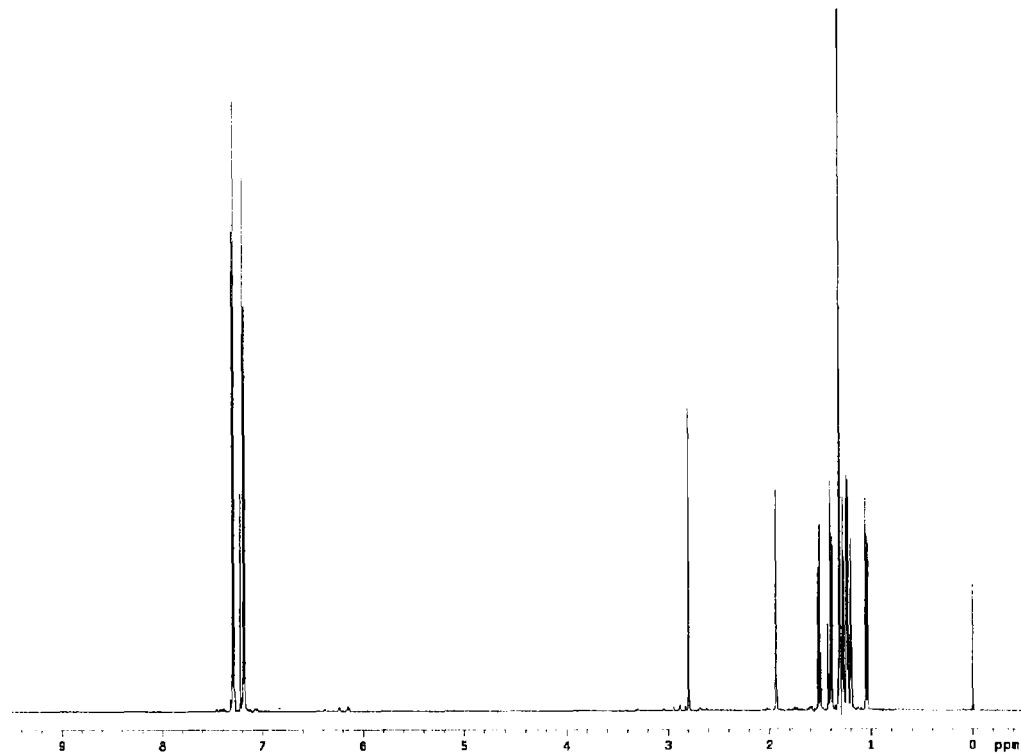
FIG. 5 is a graph of a $^1$H-NMR spectrum of Compound B obtained in Example 1.
Figure 6:
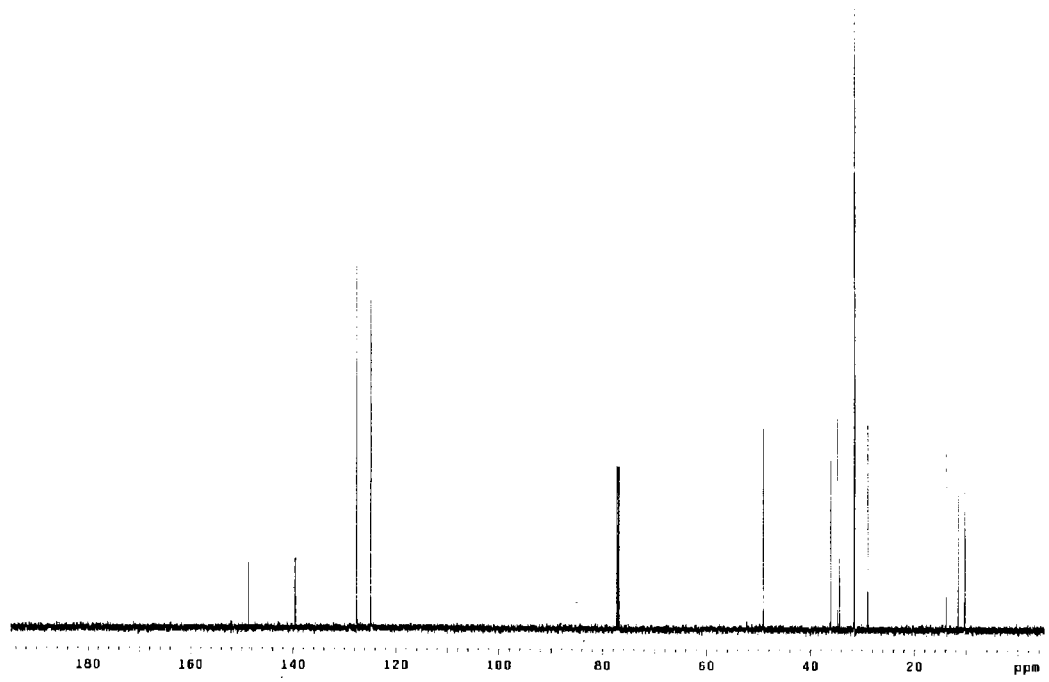
FIG. 6 is a graph of a $^{13}$C-NMR spectrum of Compound B obtained in Example 1.

Thus obtained Compound A and Compound B were each subjected to NMR for structure analysis to thereby identify the structure of the compound. FIG. 1 shows a two dimensional NMR spectrum of Compound A obtained in Example 1. FIG. 2 shows a $^1$H-NMR spectrum of Compound A obtained in Example 1. FIG. 3 shows a $^{13}$C-NMR spectrum of Compound A obtained in Example 1. FIG. 4 shows a two dimensional NMR spectrum of Compound B obtained in Example 1. FIG. 5 shows a $^1$H-NMR spectrum of Compound B obtained in Example 1. FIG. 6 shows a $^{13}$C-NMR spectrum of Compound B obtained in Example 1. From the results of such structure analysis, Compound A was found to be exo-5-(p-tert-butylphenyl)bicyclo[2.2.1]-2-heptene, and Compound B was found to be endo-5-(p-tert-butylphenyl)tricyclo[2.2.1.0$^{2,6}$]heptane.

Table 1 shows the kind of the phosphorus compound used in Example 1, the reaction temperature for the production step of the crude product, the conversion ([conversion]={[amount of 4-tert-butylbromobenzene added to reaction system]-[amount of 4-tert-butylbromobenzene remaining after reaction]}/[amount of 4-tert-butylbromobenzene added to reaction system]), and the yield of each of the compounds.

Examples 2 to 4

Each product was obtained in the same manner as in Example 1, except that a phosphorus compound described in Table 1 was used instead of 2-dicyclohexylphosphino-2'-methylbiphenyl. Note that the content ratio of each component in a reaction solution was the same as in Example 1. Table 1 shows the kind of the phosphorus compound used in each Example, the reaction temperature for the production step of each crude product, the conversions, and the yield of each compound.

TABLE 1

| | Phosphorus compound | Reaction temperature (° C.) | Conversion (%) | Yield of Compound A (%) | Yield of Compound B (%) | Yield of Compound C (%) | Yield of Compound D (%) |
|---|---|---|---|---|---|---|---|
| Example 1 | 2-dicyclohexylphosphino-2'-methylbiphenyl (structure) | 80 | 92.7 | 80.6 | 6.5 | 5.0 | 0 |

TABLE 1-continued

| | Phosphorus compound | Reaction temperature (° C.) | Conversion (%) | Yield of Compound A (%) | Yield of Compound B (%) | Yield of Compound C (%) | Yield of Compound D (%) |
|---|---|---|---|---|---|---|---|
| Example 2 | (2-biphenyl)PCy₂ | 80 | 87.0 | 78.6 | 5.8 | 2.1 | 0 |
| Example 3 | t-Bu₃P | 80 | 99.8 | 65.0 | 32.3 | 1.3 | 0 |
| Example 4 | (MeO, OMe, SO₃Na-substituted biphenyl)PCy₂ | 80 | 64.7 | 57.0 | 2.3 | 5.0 | 0 |

Comparative Examples 1 to 4

Each product for comparison was obtained in the same manner as in Example 1, except that a phosphorus compound described in the following Table 2 was used instead of 2-dicyclohexylphosphino-2'-methylbiphenyl, and that the reaction temperature condition was set to a condition described in the following Table 2. Note that the content ratio of each component in a reaction solution was the same as in Example 1. Table 2 shows the kind of the phosphorus compound used in each Comparative Example, the reaction temperature for the production step of each crude product, the conversions, and the yield of each compound.

TABLE 2

| | Phosphorus compound | Reaction temperature (° C.) | Conversion (%) | Yield of Compound A (%) | Yield of Compound B (%) | Yield of Compound C (%) | Yield of Compound D (%) |
|---|---|---|---|---|---|---|---|
| Comparative Example 1 | tri(o-tolyl)phosphine | 120 | 57.7 | 46.1 | 11.6 | 0 | 0 |
| Comparative Example 2 | (o-tolyl)P(NMe₂)₂ | 80 | 1.5 | 1.4 | 0.04 | 0 | 0 |
| Comparative Example 3 | (o-tolyl)P(pyrrolidinyl)₂ | 120 | 51.3 | 39.2 | 3.6 | 0.2 | 0 |

TABLE 2-continued

| | Phosphorus compound | Reaction temperature (° C.) | Conversion (%) | Yield of Compound A (%) | Yield of Compound B (%) | Yield of Compound C (%) | Yield of Compound D (%) |
|---|---|---|---|---|---|---|---|
| Comparative Example 4 | 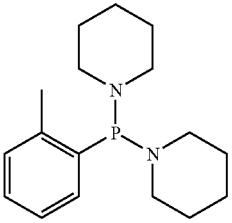 [SMILES: Cc1ccccc1P(N1CCCCC1)N1CCCCC1] | 80 | 5.3 | 4.3 | 0.3 | 0.6 | 0 |

Comparative Example 5

Figure 7:
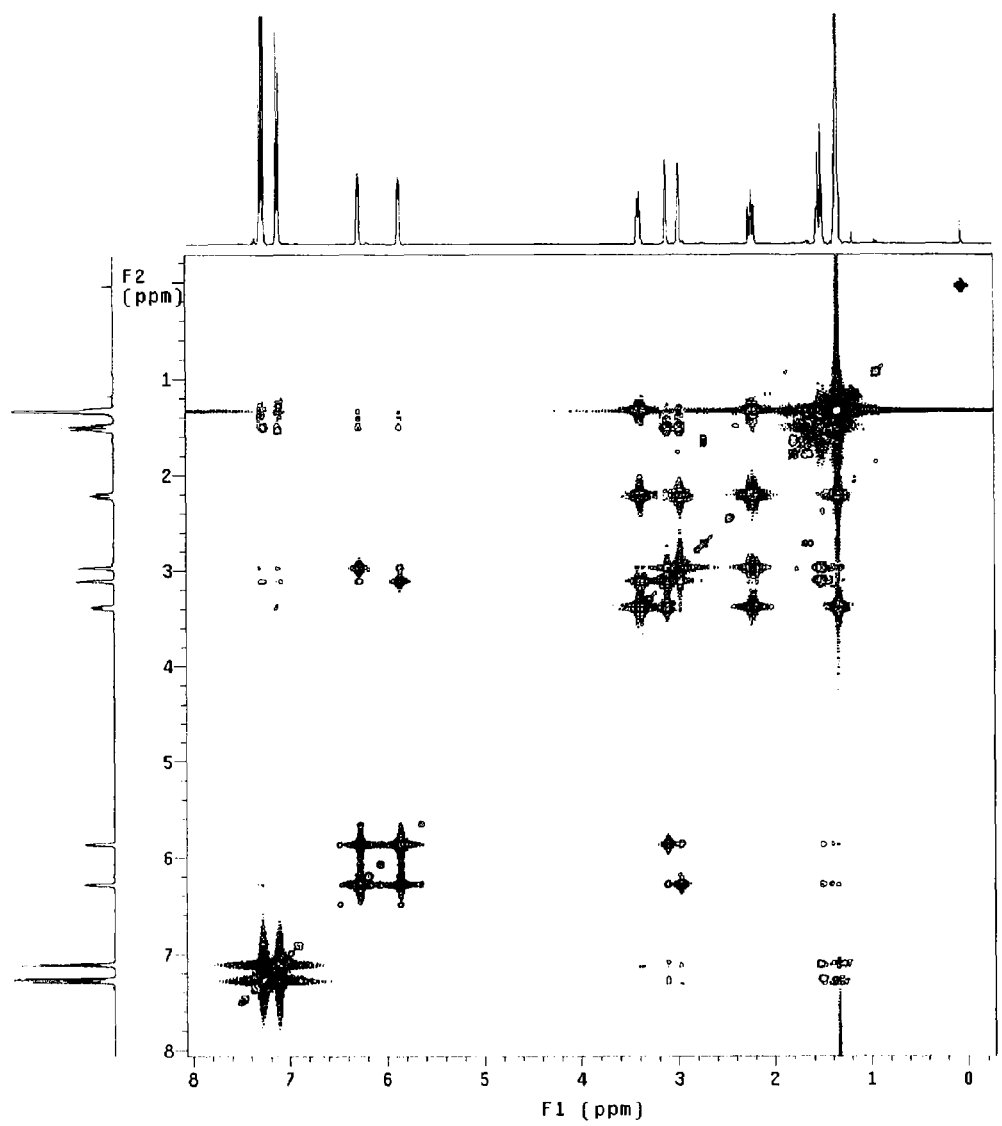
FIG. 7 is a graph of a two dimensional NMR spectrum of Compound D obtained in Comparative Example 5.
Figure 8:
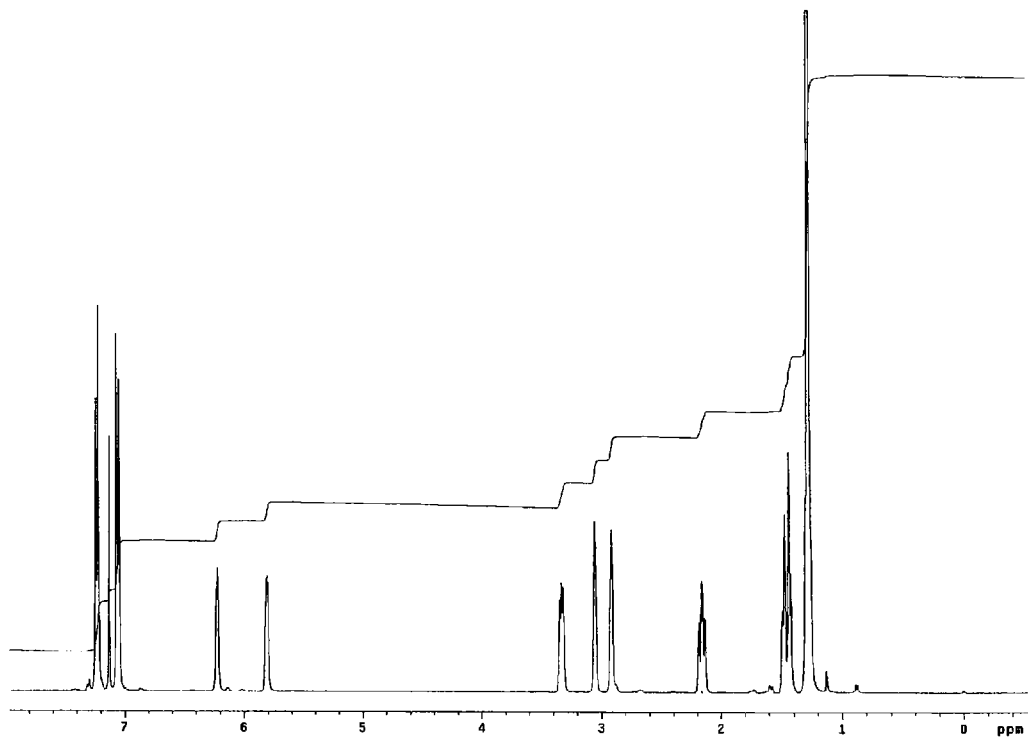
FIG. 8 is a graph of a $^1$H-NMR spectrum of Compound D obtained in Comparative Example 5.
Figure 9:
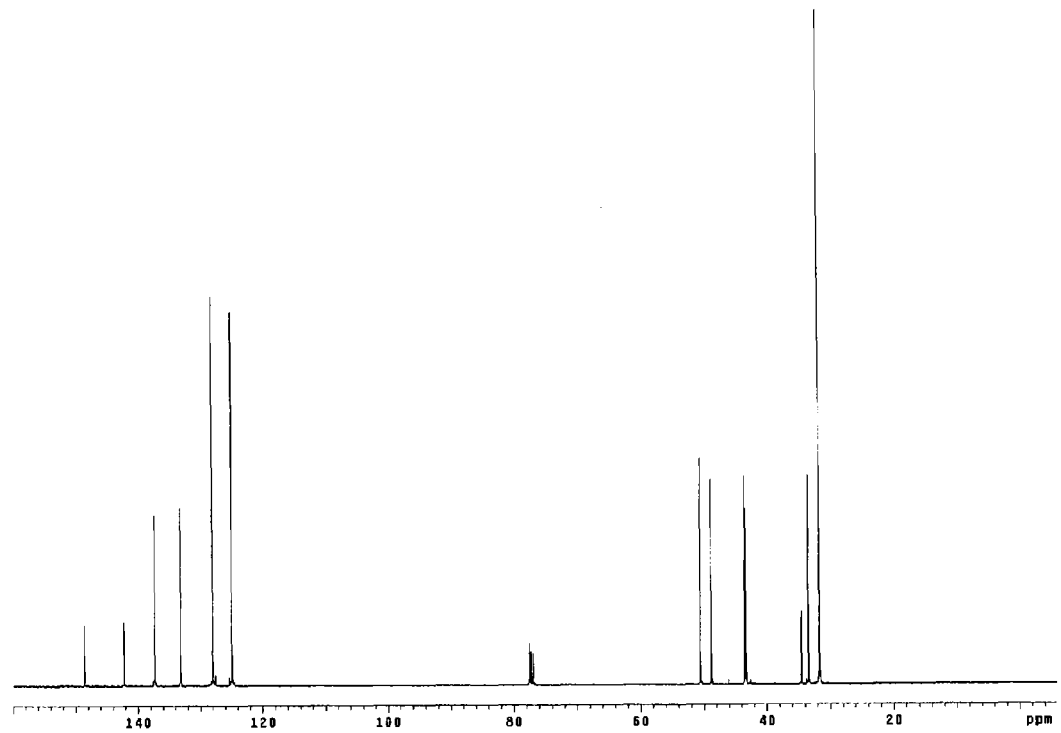
FIG. 9 is a graph of a $^{13}$C-NMR spectrum of Compound D obtained in Comparative Example 5.

Into a 2-L autoclave, 4-tBu-styrene (856 g: 5.36 mol), dicyclopentadiene (709 g: 5.36 mol), 4-tBu-catechol (44.6 g: 0.27 mol) and toluene (200 ml) were fed, and heated with stirring at 185° C. for 4 hours. The pressure was 0.4 MPa during the initial stage of the reaction. The pressure decreased with time lapse, and eventually reached 0.2 MPa. Thereafter, the heating was stopped, and the temperature in the autoclave was lowered to room temperature (25° C.) by performing natural cooling. Thereafter, the autoclave was opened, and the reaction product was taken out. Then, the obtained reaction product was purified by distillation to obtain a product as a fraction at 118 to 120° C./1 mmHg. The amount of the product yielded was 640 g (yield: 53%, based on tBu-styrene). The product was subjected to gas chromatography analysis and NMR analysis. As a result, the product was found to be a mixture of an endo isomer and an exo isomer of 5-(p-t-butylphenyl)bicyclo[2.2.1]-2-heptene (isomer ratio=79/21). Next, a part of the mixture (1.2 g) was subjected to separation and purification on a recycling preparative HPLC (manufactured by Japan Analytical Industry Co., Ltd., LC-918). One of the isomers was obtained at a purity of 97.1% (yield: 0.23 g). Thus obtained isomer was subjected to structure analysis by NMR. As a result, the obtained isomer was found to be endo-5-(p-t-butylphenyl)bicyclo[2.2.1]-2-heptene (Compound D). Accordingly, the obtained product was found to be 5-(p-t-butylphenyl)bicyclo[2.2.1]-2-heptene where endo/exo=79/21. Note that FIG. 7 shows a two dimensional NMR spectrum of Compound D obtained in Comparative Example 5, FIG. 8 shows a $^1$H-NMR spectrum of Compound D obtained in Comparative Example 5, and FIG. 9 shows a $^{13}$C-NMR spectrum of Compound D obtained in Comparative Example 5.

As is apparent from the results shown in Table 1, it was found out that endo-5-(p-t-butylphenyl)bicyclo[2.2.1]-2-heptene (Compound D) did not exist in the products (Examples 1 to 4) obtained by employing the method for producing a norbornene derivative of the present invention. Therefore, it was confirmed that the method for producing a norbornene derivative of the present invention succeeded in selectively producing exo-5-(p-tert-butylphenyl)bicyclo[2.2.1]-2-heptene (Compound A). As is apparent from the results shown in Table 1, according to the method for producing a norbornene derivative of the present invention, it was also confirmed to be able to produce Compound A at a sufficiently high yield.

Meanwhile, as is apparent from the results shown in Table 2, it was found out that, in a case (Comparative Examples 1 to 4) where one shown in Table 2 was used as the phosphorus compound, the yields of Compound A were not sufficient. As is apparent from the analysis result of the product obtained in Comparative Example 5, it was found out that, in a case (Comparative Example 5) where the Diels-Alder reaction was used, Compound A failed to be produced selectively.

Example 5

Into a 0.1-L three-necked flask, tri-tert-butyl phosphorus (a phosphorus compound [the same phosphorus compound as that used in Example 3]:14.3 mg: 0.071 mmol), palladium acetate (1.3 mg: 0.006 mmol), dimethylsulfoxide (DMSO: 25 ml), norbornadiene (1.8 ml: 19.0 mmol), 4-tert-butylbromobenzene (1.0 ml: 5.9 mmol), sodium hydroxide (NaOH: 0.77 g: 19.2 mmol), and formic acid (0.6 ml: 15.4 mmol) was fed under a nitrogen atmosphere, and then heated with stirring under a temperature condition of 80° C. for 4 hours to thereby obtain a reaction solution. Note that, in such a reaction solution, the content ratio of palladium acetate to 4-tert-butylbromobenzene was 0.1% by mole, the content ratio of the phosphorus compound to 4-tert-butylbromobenzene was 1.2% by mole, the molar equivalent of norbornadiene to the 4-tert-butylbromobenzene was 3.22 equivalent, the molar equivalent of NaOH to 4-tert-butylbromobenzene was 3.25 equivalent, and the molar equivalent of formic acid to the 4-tert-butylbromobenzene was 2.61 equivalent.

Next, the reaction solution was cooled to 25° C., and then poured into 30 ml of ice water. By using a separatory funnel, extraction was performed with n-hexane (5 ml×3 times) to obtain a n-hexane solution. Subsequently, the n-hexane solution was washed with water and a saturated sodium chloride solution. Then, the washed n-hexane solution was dried with anhydrous magnesium sulfate, filtered and concentrated. Thus, a crude product (1.2 g) was obtained.

Then, the obtained crude product was subjected to gas chromatography analysis. As a result, the obtained product was found to be a mixture containing Compounds A to C in the above-described Reaction Formula (II), as in the case of the crude product obtained in Example 1.

The thus obtained crude product was purified by distillation to obtain a product as a fraction at 104° C./1 mmHg. The amount of such a product yielded was 1.1 g (yield 82.6%). The obtained product was subjected to gas chromatography analysis. As a result, the obtained product was found to be a mixture containing Compound A (yield: 55.3%) and Compound B (yield: 27.3%).

Table 3 shows the kind of the base used in this example, the reaction temperature for the production step of the crude product, the conversion ([conversion]={[amount of 4-tert-butylbromobenzene added to reaction system]-[amount of 4-tert-butylbromobenzene remaining after reaction]}/[amount of 4-tert-butylbromobenzene added to reaction system]), and the yield of each of Compounds A to D in the above-described Reaction Formula (II).

Examples 6 to 11

Each product was obtained in the same manner as in Example 5, except that the base used was changed from sodium hydroxide to a base described in the following Table 3, and that the content of the base to the bromine compound was changed to the ratio described in the following Table 3. Note that the content ratio of each component other than the base in a reaction solution was the same as in Example 5. Each of the products thus obtained was subjected to gas chromatography analysis. Table 3 shows the kind of the base used in each Example, the reaction temperature for the production step of the crude product, the conversions, and the yield of each compound.

TABLE 3

|  | Base (Equivalent to bromine compound) | Reaction temperature (° C.) | Conversion (%) | Yield of Compound A (%) | Yield of Compound B (%) | Yield of Compound C (%) | Yield of Compound D (%) |
|---|---|---|---|---|---|---|---|
| Example 5 | NaOH (3.25) | 80 | 99.4 | 55.3 | 27.3 | 0.8 | 0 |
| Example 6 | $Na_2CO_3$ (3.25) | 80 | 100 | 50.9 | 31.5 | 1.2 | 0 |
| Example 7 | $K_2CO_3$ (3.25) | 80 | 100 | 60.1 | 26.0 | 6.4 | 0 |
| Example 8 | KOH (3.25) | 80 | 99.4 | 74.2 | 10.2 | 3.5 | 0 |
| Example 9 | KOH (1.05) | 80 | 78 | 51.0 | 22.2 | 1.2 | 0 |
| Example 10 | KOH (4.20) | 80 | 70 | 52.3 | 4.7 | 3.5 | 0 |
| Example 11 | KOH (5.25) | 80 | 60 | 50.6 | 3.0 | 3.0 | 0 |

As is apparent from the results shown in Table 3 and the results of Example 3 in Table 1, by considering the reaction systems (Example 3 and Examples 5 to 11) where tri-tert-butyl phosphorus was used as the phosphorus compound, it is found that, in the cases (Examples 5 to 11) where an alkali metal salt or an alkali metal hydroxide was used as the base, the production of Compound B was more inhibited. According to these results, it was found to be able to inhibit sufficiently the production of the by-products, by coexisting an alkali metal salt or an alkali metal hydroxide as a base in a reaction system. Meanwhile, regarding the reaction systems where tri-tert-butyl phosphorus was used as the phosphorus compound, by considering the cases (Example 3 and Examples 5 to 8) where each of the reaction solutions contained a base at the same molar equivalent, it is found that, in the case (Example 7) where potassium hydroxide (KOH) was used as the base, production of the by-products was able to be more highly inhibited and the yield of the target norbornene derivative (Compound A) was able to be more improved. Moreover, by considering the cases (Examples 8 to 11) where the content of KOH was varied, it is found that the larger value the molar equivalent of KOH to the bromine compound took, the higher level the inhibition in production of the by-products reached. As a result, it was found that, in order to achieve improvement in conversion and yield and also inhibition of production of the by-products at a higher level in a balanced manner, the value of the molar equivalent of KOH to the bromine compound (content of KOH) was preferably set to 1 equivalent or more.

INDUSTRIAL APPLICABILITY

As has been described above, according to the present invention, it is possible to provide a method for producing a norbornene derivative capable of selectively producing, at a sufficiently high yield, a specific norbornene derivative (exo isomer) in which the configuration of a substituent such as a substituted phenyl group is an exo configuration.

Therefore, the method for producing a norbornene derivative of the present invention is useful as a method for producing a norbornene derivative which has a peculiar structure and which can be suitably used for producing optical disks, magneto-optical discs, optical lenses, spectacle lenses, optical films, and the like.

The invention claimed is:
1. A method for producing a norbornene derivative, wherein,
in the presence of a reducing agent, palladium and at least one selected from phosphorus compounds represented by the following formulas (1) and (2):

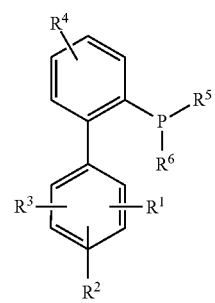

(1)

wherein, in formula (1), $R^1$, $R^2$, $R^3$ and $R^4$ each independently represent any one selected from an hydrogen atom, a linear chain saturated hydrocarbon group having 1 to 10 carbon atoms, a branched chain saturated hydrocarbon group having 3 to 10 carbon atoms, a cyclic saturated hydrocarbon group having 3 to 8 carbon atoms, a dialkylamino group having 1 to 10 carbon atoms, an alkoxy group having 1 to 10 carbon atoms and an alkali metal sulfonate group, and $R^5$ and $R^6$ each independently represents any one selected from a branched chain saturated hydrocarbon group having 3 to 10 carbon atoms, a cyclic saturated hydrocarbon group having 3 to 8 carbon atoms, a phenyl group, a tolyl group, a biphenyl group and a naphthyl group, and

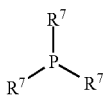  (2)

wherein, in formula (2), $R^7$ represents a branched chain saturated hydrocarbon group having 3 to 10 carbon atoms,
a norbornadiene derivative represented by the following formula (3):

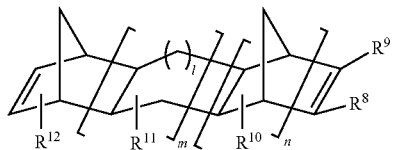  (3)

wherein, in formula (3), $R^8$, $R^9$, $R^{10}$, $R^{11}$ and $R^{12}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms, l represents an integer of 0 or 1, m represents an integer of 0 or 1, and n represents an integer of 0 or 1, and a bromine compound represented by the following formula (4):

Br—Z—$R^{13}$  (4)

wherein, in formula (4), Z represents a phenylene group and $R^{13}$ represents a branched chain hydrocarbon group having 3 to 10 carbon atoms, are reacted with each other to thereby obtain a norbornene derivative represented by the following formula (5)

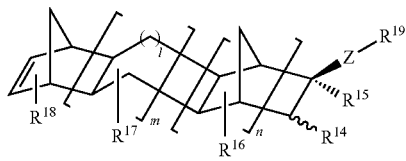  (5)

wherein, in formula (5), $R^{14}$, $R^{15}$, $K^{16}$, $R^{17}$ and $R^{18}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms, Z represents a phenylene group, $R^{19}$ represents a branched chain hydrocarbon group having 3 to 10 carbon atoms, l represents an integer of 0 or 1, m represents an integer of 0 or 1, and n represents an integer of 0 or 1, the norbornene derivative having a configuration of a substituent represented by Z in formula (5) that is an exo configuration.

2. The method for producing a norbornene derivative according to claim 1, wherein, in formula (1),
$R^1$, $R^2$, and $R^3$ are each independently any one selected from a linear chain saturated hydrocarbon group having 1 to 3 carbon atoms, an alkoxy group having 1 to 3 carbon atoms and an alkali metal sulfonate group,
$R^4$ is a hydrogen atom, and
$R^5$ and $R^6$ are each independently a cyclic saturated hydrocarbon group having 5 to 8 carbon atoms.

3. The method for producing a norbornene derivative according to claim 1, wherein, in formula (2), $R^7$ is a branched chain saturated hydrocarbon group having 3 to 5 carbon atoms.

4. The method for producing a norbornene derivative according to claim 1, wherein, in each of formulas (3) and (5), m is 0, and n is 0.

5. The method for producing a norbornene derivative according to claim 1, wherein when the norbornadiene derivative and the bromine compound are reacted with each other, their reaction is conducted in the additional presence of a base.

6. The method for producing a norbornene derivative according to claim 5, wherein the base is at least one selected from an alkali metal salt and an alkali metal hydroxide.

7. The method for producing a norbornene derivative according to claim 5, wherein the base is at least one selected from NaOH, $Na_2CO_3$, KOH and $K_2CO_3$.

8. The method for producing a norbornene derivative according to claim 5, wherein a content of the base is in an amount such that the content of the base to a content of the bromine compound is in a molar ratio in a range from 1:1 to 10:1.

9. The method according to claim 1, wherein l is 0.

10. The method according to claim 1, wherein said reducing agent comprises a member selected from the group consisting of formic acid, an alkali metal salt of formic acid, an allkaline earth metal salt of formic acid, and an ammonium salt of formic acid.

11. The method according to claim 1, wherein said reducing agent comprises a metal salt of formic acid.

12. The method according to claim 1, wherein said reducing agent comprises zinc or sodium borohydride.

13. A method for producing a norbornene derivative represented by the following formula (5):

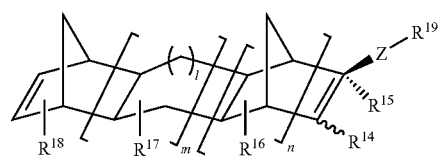  (5)

wherein, in formula (5), $R^{14}$, $R^{15}$, $K^{16}$, $R^{17}$ and $R^{18}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms, Z represents a phenylene group, $R^{19}$ represents a branched chain hydrocarbon group having 3 to 10 carbon atoms, l represents an integer of 0 or 1, m represents an integer of 0 or 1, and n represents an integer of 0 or 1, wherein the norbornene derivative has a configuration of a substituent represented by Z in formula (5) that is an exo configuration, said method comprising (a) allowing a norbornadiene derivative represented by the following formula (3):

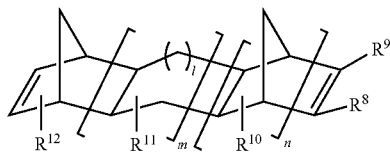

(3)

wherein, in formula (3), $R^8$, $R^9$, $R^{10}$, $R^{11}$ and $R^{12}$ each independently represent any one selected from a hydrogen atom, a fluorine atom, a chlorine atom, a linear chain hydrocarbon group having 1 to 10 carbon atoms and a branched chain hydrocarbon group having 3 to 10 carbon atoms, l represents an integer of 0 or 1, m represents an integer of 0 or 1, and n represents an integer of 0 or 1, and a bromine compound represented by the following formula (4):

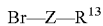

(4)

wherein, in formula (4), Z represents a phenylene group, and $R^{13}$ represents a branched chain hydrocarbon group having 3 to 10 carbon atoms, to react with each other in a reaction solution, said reaction solution being obtained by introducing said norbornadiene derivative, said bromine compound, a reducing agent, a base, a palladium compound and at least one selected from phosphorus compounds represented by the following formulas (1) and (2):

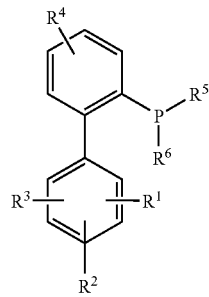

(1)

wherein, in formula (1), $R^1$, $R^2$, $R^3$ and $R^4$ each independently represent any one selected from an hydrogen atom, a linear chain saturated hydrocarbon group having 1 to 10 carbon atoms, a branched chain saturated hydrocarbon group having 3 to 10 carbon atoms, a cyclic saturated hydrocarbon group having 3 to 8 carbon atoms, a dialkylamino group having 1 to 10 carbon atoms, an alkoxy group having 1 to 10 carbon atoms and an alkali metal sulfonate group, and $R^5$ and $R^6$ each independently represents any one selected from a branched chain saturated hydrocarbon group having 3 to 10 carbon atoms, a cyclic saturated hydrocarbon group having 3 to 8 carbon atoms, a phenyl group, a tolyl group, a biphenyl group and a naphthyl group, and

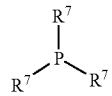

(2)

wherein, in formula (2), $R^7$ represents a branched chain saturated hydrocarbon group having 3 to 10 carbon atoms, to form a reaction solution in a solvent, wherein the reducing agent and the bromine compound are introduced in a molar ratio in the range of 1:1 and 1:10, and the base and the bromine compound are introduced in a molar ratio in the range of 1:1 to 10:1.

14. The method according to claim 13, wherein the reducing agent and the bromine compound are introduced in a molar ratio of 1:1 to 1:5.

* * * * *